(12) United States Patent
Sekido

(10) Patent No.: US 12,082,784 B2
(45) Date of Patent: Sep. 10, 2024

(54) ELECTRONIC MODULE, METHOD OF MANUFACTURING ELECTRONIC MODULE, AND ENDOSCOPE

(71) Applicant: OLYMPUS CORPORATION, Tokyo (JP)

(72) Inventor: Takanori Sekido, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 169 days.

(21) Appl. No.: 17/993,425

(22) Filed: Nov. 23, 2022

(65) Prior Publication Data

US 2023/0093501 A1 Mar. 23, 2023

Related U.S. Application Data

(63) Continuation of application No. PCT/JP2020/024893, filed on Jun. 24, 2020.

(51) Int. Cl.
*A61B 1/05* (2006.01)
*A61B 1/00* (2006.01)
*G02B 23/24* (2006.01)

(52) U.S. Cl.
CPC ............ *A61B 1/05* (2013.01); *G02B 23/2484* (2013.01); *A61B 1/0011* (2013.01)

(58) Field of Classification Search
CPC ..... A61B 1/05; A61B 1/0011; A61B 1/00114; A61B 1/051; G02B 23/2484; Y02P 70/50; H01L 25/18; H01L 27/146; H05K 1/02

(Continued)

(56) References Cited

U.S. PATENT DOCUMENTS 10,842,365 B2 * 11/2020 Kojima ................. A61B 1/05
11,918,179 B2 * 3/2024 Nakagawa ........... A61B 1/0011
(Continued)

FOREIGN PATENT DOCUMENTS

JP 2003-017367 A 1/2003
JP 2011-228485 A 11/2011
(Continued)

OTHER PUBLICATIONS

International Search Report dated Sep. 1, 2020 received in PCT/JP2020/024893.

*Primary Examiner* — Tung T Vo
(74) *Attorney, Agent, or Firm* — Scully, Scott, Murphy & Presser, P.C.

(57) ABSTRACT

An electronic module includes: an integrated circuit including a first mounting surface; a solid wiring board including a second mounting surface and a third mounting surface within a horizontally projected area corresponding to the integrated circuit; both the second and third mounting surfaces face the first mounting surface of the integrated circuit and disposed at positions with different distances to the first mounting surface. An electrode surface of an electronic component mounted in a space formed between the first and the third mounting surfaces, and an electrode surface of the second mounting surface are arranged substantially parallel to a surface of the integrated circuit on which electrodes are aligned. The electrode on the second mounting surface and the electrodes of the integrated circuit are electrically connected to each other. The electrode of the electronic component is electrically connected to the electronic component and the electrodes of the integrated circuit.

10 Claims, 9 Drawing Sheets

(58) Field of Classification Search
USPC .......................................................... 348/65
See application file for complete search history.

(56) References Cited

U.S. PATENT DOCUMENTS

| | | |
|---|---|---|
| 2019/0038117 A1 | 2/2019 | Motohara et al. |
| 2019/0069767 A1 | 3/2019 | Mikami et al. |
| 2019/0261839 A1* | 8/2019 | Sakai ........................ H01L 27/14 |
| 2019/0267416 A1* | 8/2019 | Kohama ................. H04N 25/75 |
| 2021/0219830 A1* | 7/2021 | Nakagawa ............. A61B 1/051 |
| 2022/0102330 A1* | 3/2022 | Onoko ................. H05K 3/3431 |
| 2022/0341780 A1* | 10/2022 | Kasahara .............. G01J 3/0297 |

FOREIGN PATENT DOCUMENTS

| | | |
|---|---|---|
| JP | 5530055 B2 | 6/2014 |
| JP | 2017-023234 A | 2/2017 |
| JP | 2019-166170 A | 10/2019 |
| JP | 6612264 B2 | 11/2019 |
| WO | 2017/195605 A1 | 11/2017 |
| WO | 2017/199406 A1 | 11/2017 |

* cited by examiner

ELECTRONIC MODULE, METHOD OF MANUFACTURING ELECTRONIC MODULE, AND ENDOSCOPE

CROSS-REFERENCE TO RELATED APPLICATION

This application is a continuation application of PCT/JP2020/024893 filed on Jun. 24, 2020, the entire contents of which are incorporated herein by this reference.

BACKGROUND OF THE INVENTION

1. Field of the Invention

The present invention relates to an electronic module which is highly reliable while being compact and highly integrated with a simple configuration, a method of manufacturing the electronic module, and an endoscope.

2. Description of the Related Art

In recent years, a spread of mobile terminals has accelerated a trend of miniaturization of electronic components, which encourages a proposal for a technique of pursuing miniaturization of the electronic components by imparting a predetermined function to a board on which the electronic components are mounted. For example, Japanese Patent Application Laid-Open Publication No. 2003-17367 proposes a stacked electronic component configured by stacking a plurality of electronic components, and including external electrodes on both end portions of the electronic components.

SUMMARY OF THE INVENTION

An electronic module according to one aspect of the present invention includes: an integrated circuit including a first mounting surface having a first mounting area; and a solid wiring board including a second mounting surface and a third mounting surface, the second mounting surface having a second mounting area smaller than the first mounting area, the third mounting surface having a third mounting area equal to or smaller than a difference between the first mounting area and the second mounting area, the second mounting surface and the third mounting surface being arranged within a horizontally projected area corresponding to the integrated circuit when the integrated circuit is viewed from a direction perpendicular to the first mounting surface. Both the second mounting surface and the third mounting surface face the first mounting surface of the integrated circuit, and are disposed at positions with different distances to the first mounting surface, a surface of an electrode of an electronic component mounted in a space formed between the first mounting surface and the third mounting surface, and a surface of an electrode on the second mounting surface are arranged substantially parallel to a surface of the integrated circuit on which electrodes are aligned, the electrode on the second mounting surface and the electrodes of the integrated circuit are electrically connected to each other; and the electrode of the electronic component is electrically connected to the electronic component and the electrodes of the integrated circuit.

A manufacturing method of an electronic module according to one aspect of the present invention is a method for electrically connecting a solid wiring board to a first member, the first member including a first mounting surface on which a plurality of soldering lands are arranged, the solid wiring board including a second mounting surface and a third mounting surface, on each of which a plurality of soldering lands are arranged, each of the second mounting surface and third mounting surface facing the first mounting surface and having a different distance to the first mounting surface. The method includes: mounting an electronic component in a space created by a difference between a distance from the second mounting surface to the first mounting surface and a distance from the third mounting surface to the first mounting surface; fixing the electronic component mounted in the space by a resin; and electrically connecting the soldering lands on the first mounting surface, the soldering lands on each of the second mounting surface and the third mounting surface, and an electrode of the electronic component.

An electronic module according to another aspect of the present invention includes: an image pickup device connected to an objective optical system; a relay circuit board connected to the image pickup device and including an external connecting terminal; a cable connecting board connected to the relay circuit board and including a transmission cable connecting terminal; and a transmission cable connected to the cable connecting board. The relay circuit board and the cable connecting board are connected to each other through a first electronic component, the first electronic component includes a plurality of electronic components each having a different size, the cable connecting board includes a plurality of planes each having a different distance to a surface of the relay circuit board to which the cable connecting board faces, an electronic component mounting electrode and a board connecting electrode are disposed on each of the planes, a second electronic component is mounted on an electronic component mounting electrode of the relay circuit board, a surface of the board connecting electrode and a surface of a relay-circuit-board-side electrode of the first electronic component are located on a substantially same surface, and the board connecting electrode and the relay-circuit-board-side electrode of the first electronic component are connected to a board connecting electrode of the relay circuit board.

An endoscope according to one aspect of the present invention includes an electronic module. The electronic module includes: an integrated circuit including a first mounting surface having a first mounting area; and a solid wiring board including a second mounting surface and a third mounting surface, the second mounting surface having a second mounting area smaller than the first mounting area, the third mounting surface having a third mounting area equal to or smaller than a difference between the first mounting area and the second mounting area, the second mounting surface and the third mounting surface being arranged within a horizontally projected area corresponding to the integrated circuit when the integrated circuit is viewed from a direction perpendicular to the first mounting surface. Both the second mounting surface and the third mounting surface face the first mounting surface of the integrated circuit, and are disposed at positions with different distances to the first mounting surface, a surface of an electrode of an electronic component mounted in a space formed between the first mounting surface and the third mounting surface, and a surface of an electrode on the second mounting surface are arranged substantially parallel to a surface of the integrated circuit on which electrodes are aligned, the electrode on the second mounting surface and the electrodes of the integrated circuit are electrically connected to each other, and the electrode of the electronic component is electrically connected to the electronic component and the electrodes of the integrated circuit.

DETAILED DESCRIPTION OF THE PREFERRED EMBODIMENT(S)

Figure 1:
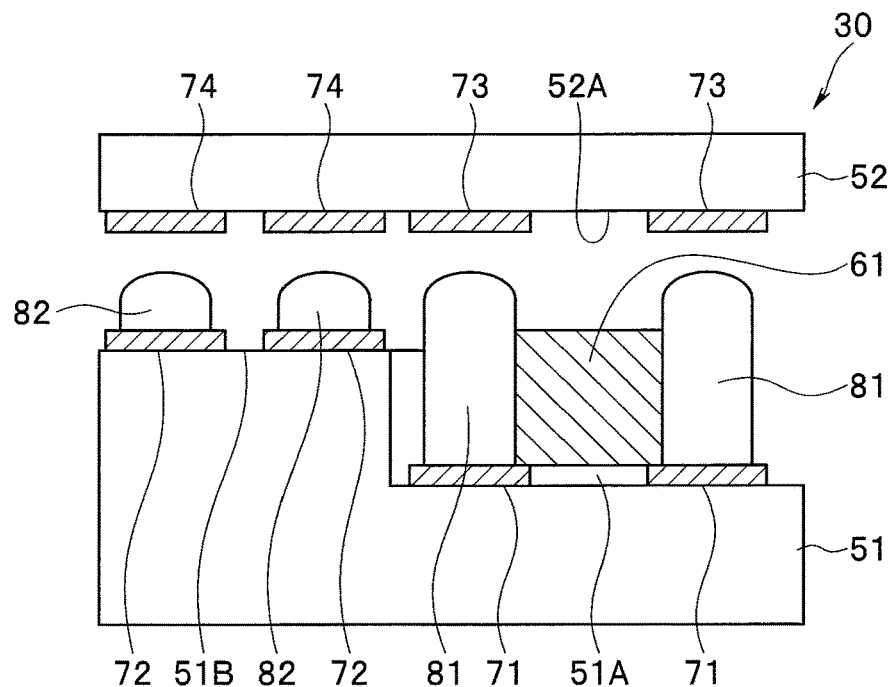
FIG. 1 is a side view showing an electronic module according to a first embodiment of the present invention.

Hereinafter, embodiments of the present invention will be described with reference to drawings.

Note that there is a case where a different scale size is used for each of the constituent elements in the drawings to be used for the description below in order to allow each of the constituent elements to be illustrated in a recognizable size in each of the drawings, and the present invention is not limited only to the number, shapes, ratio of a size of a certain constituent element to sizes of other constituent elements, and a relative positional relationship among the constituent elements shown in these drawings.

First Embodiment

An electronic module according to the present first embodiment will be described with reference to FIG. 1. FIG. 1 is a side view showing the electronic module according to the first embodiment of the present invention.

An electronic module 30 according to the present first embodiment includes a solid wiring board 51. The solid wiring board 51 on which various electronic components are mounted may be formed by what is called an MID (molded interconnect device) technology. Note that MID refers to a three-dimensional molded interconnect device in which an electric circuit is integrally formed on a surface of a solid molded product such as an injection molded product. Unlike a conventional two-dimensional circuit, such an MID technology enables a circuit to be added on an inclined surface, a perpendicular surface, a curved surface, an inner surface of a through hole formed in a molded body, or the like. In addition, the solid wiring board 51 may be fabricated as a solid board having a similar configuration by using a 3D printer or the like.

The known micro-composite processing technology can be used in the MID technology. With the micro-composite processing technology, it is possible to achieve a 3D mounting device on which fine patterning and bare chip mounting can be performed, by using a molded surface activation processing technology, a laser patterning method, and the like in the MID technology for forming an electric circuit on an injection molded product.

As shown in FIG. 1, the solid wiring board 51 is formed by the above-described MID technology. The solid wiring board 51 includes a second mounting surface 51B and a third mounting surface 51A that face a mounting surface (first surface, first mounting surface) 52A. The second mounting surface 51B includes no component mounted thereon and is electrically connected to the first mounting surface. The third mounting surface 51A is a surface for component mounting and has a step in a height direction with respect to the second mounting surface.

First electrodes 71 are formed on the third mounting surface 51A by a laser processing method and the like. Similarly as described above, second electrodes 72 are formed on the second mounting surface 51B by the laser processing method and the like.

A space created by the height difference between the third mounting surface 51A and the second mounting surface 51B can serve as a space suitable for mounting an electronic component (first chip component) 61, as shown in the drawings, when an integrated circuit 52, which has a relatively large mounting area, is mounted to the second mounting surface (when the second mounting surface is electrically connected to the first mounting surface 52A). The first chip component 61 is, for example, a capacitor, a resistor, a jumper component, or the like.

Electrodes of the first chip component 61 may be electrically connected to electrodes 73 of the integrated circuit 52 to ensure a specific electronic circuit function. For example, disposing the first chip component 61, as a capacitor, between the integrated circuit 52 and a power source terminal of the solid wiring board enables a noise removal performance to be ensured.

Furthermore, the first chip component 61 is connected, by solder 81, to the electrodes provided on the third mounting surface 51A of the solid wiring board 51. The electrodes 73 of the integrated circuit 52 and the electrodes provided on the third mounting surface 51A of the solid wiring board 51 may be electrically connected to each other through a first chip component electrode 82 or the solder 81.

In other words, at this time, a terminal (corresponding to the upper end position of the solder 81 in FIG. 1), which is arranged on a side away from the third mounting surface 51A for mounting the first chip component 61, is electrically connected to the integrated circuit 52, and also the electrodes 82 on the second mounting surface 51B are electrically connected to the integrated circuit 52.

Such a configuration can provide a compact electronic module which is configured such that the solid wiring board 51 is arranged, with the area of the mounting portion thereof not being expanded, within the area of the integrated circuit 52 which is a component occupying the largest area (the mounting area including the terminal portion of the integrated circuit 52, which is required for mounting the integrated circuit 52), that is, within a horizontally projected area of the integrated circuit 52 when viewing the integrated circuit 52 from a direction perpendicular to the mounting surface of the integrated circuit 52.

Thus, the shape of the mounting portion of the solid wiring board 51 is contrived, while achieving the electric connection of the first chip component 61 and the solid wiring board 51 to the integrated circuit 52 that requires a first mounting area. Specifically, the way of housing the chip component is contrived by providing the second mounting surface 51B having a second mounting area smaller than the first mounting area occupied by the integrated circuit 52 when the integrated circuit 52 is mounted, and the third mounting surface 51A which is an area equal to or smaller than a difference between the first mounting area and the second mounting area.

In other words, both the second mounting surface and the third mounting surface face the mounting surface of the integrated circuit 52, and the second mounting surface and the third mounting surface each have a different distance to the mounting surface of the integrated circuit 52. Furthermore, the electronic component (chip component 61) is mounted in the space between the mounting surface of the integrated circuit 52 and the third mounting surface (the upper portion of the third mounting surface 51A in FIG. 1).

The alignment of the electrodes of the electronic component mounted on the third mounting surface 51A and the electrodes 82 on the second mounting surface 51B is substantially parallel to the surface of the integrated circuit 52 on which the electrodes 73 and 74 are aligned. Therefore, the electrodes of the electronic component and the electrodes 73 and 74 on the first mounting surface are parallel to each other. Such a configuration facilitates the electric connection between the solid wiring board 51 and the integrated circuit 52. In addition, such a configuration achieves the compact electronic module in which other components are fitted in a range within the area of the integrated circuit 52 in the direction of the mounting surface thereof.

Second Embodiment

Next, with reference to FIG. 2, description will be made on an embodiment in which the above-described integrated circuit 52 is used as a relay circuit board on which an image pickup chip is mounted. The image pickup chip includes an image pickup device 31 and a stacked image pickup optical system 32, for example. Note that, as described above, the present second embodiment is an example in which the integrated circuit denoted by the reference sign 52 in the first embodiment is used as the relay circuit board. Therefore, in the description of the present second embodiment, the reference sign 52 indicates the relay circuit board 52.

Figure 2:
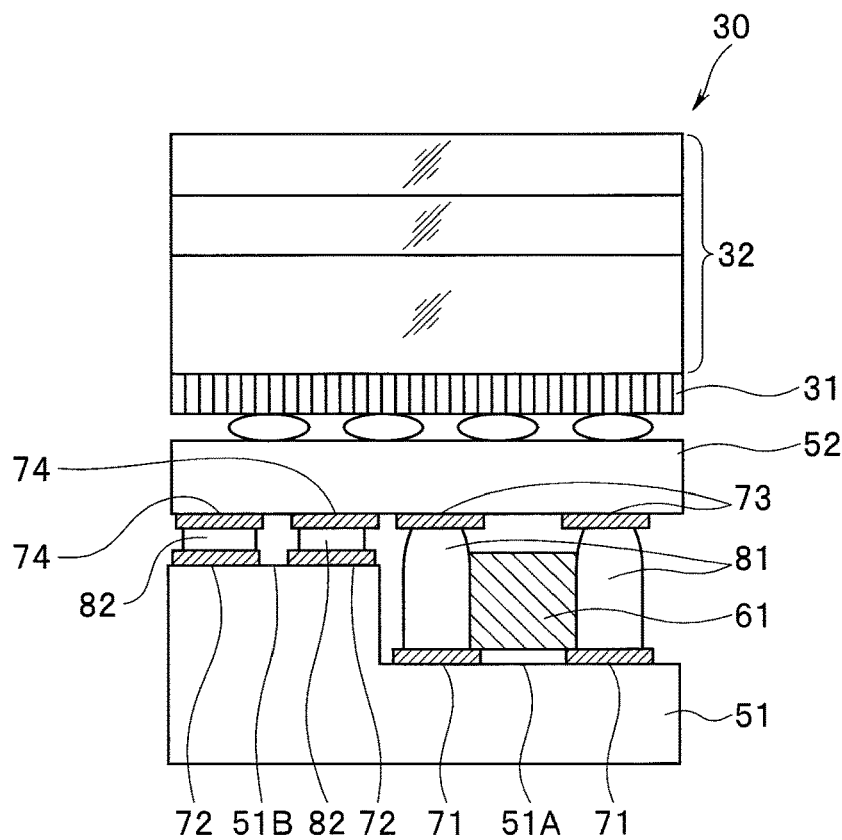
FIG. 2 is a side view showing an electronic module according to a second embodiment of the present invention.

As shown in FIG. 2, in the second embodiment, for example, the image pickup chip is supposed to be formed by stacking the image pickup optical system on the image pickup device 31 at a wafer stage of the image pickup device 31, and dicing and separating the wafer. Thus, there is no component or member protruding from the area of the image pickup surface of the image pickup device 31 in the expanding direction (the lateral direction and the depth direction of the image pickup plane and the paper surface), to thereby be capable of providing the compact electronic module 30 with a simple configuration.

The image pickup device 31 is a device including, on the image pickup surface thereof, a plurality of light-receiving elements, and configured to convert an object image received from the image pickup optical system 32 into an electric signal. Due to high-pixelation and high-sensitivity, such kind of device has a tendency to increase in the size of the area of the light-receiving portion on which sensors are laid two-dimensionally. As a result, the area required for mounting (mounting area) of such a device becomes larger than those of other components, and the device is likely to occupy a dominant space in the module. Therefore, a design for not allowing other components to protrude outside of the mounting area of the image pickup device is one of criteria of miniaturization (in the direction of mounting area, in particular) of the electronic module (also referred to as image pickup module).

In the present second embodiment, the relay circuit board 52 (as described above, the reference sign 52 indicates the relay circuit board in the description of the present second embodiment) constitutes a part of the image pickup module 30, and the relay circuit board 52 is interposed between the solid wiring board 51 and the image pickup device 31. Providing the relay circuit board 52 enables a signal line for the image pickup device 31 to be connected to the electrodes of the solid wiring board 51 or the first chip component 61, which are located at positions different from the position where the electrodes of the image pickup device 31 are aligned, to thereby enable a freedom in the wiring and component layout to be obtained.

The relay circuit board 52 includes a plane that faces the third mounting surface 51A and the second mounting surface 51B in the solid wiring board 51, and on the same plane, third electrodes 73 and fourth electrodes 74 are disposed. The third electrodes 73 are connected to the electrodes of the first chip component 61 which is a first electronic component connected to the first electrodes 71, and the fourth electrodes 74 are connected to the second electrodes 72.

Note that the height of the first chip component 61 as the above-described first electronic component, that is, the height dimension of the first chip component 61 in a direction perpendicular to the surface direction of the image pickup plane of the image pickup device 31 is designed to be substantially equal to that of the step created by the height difference between the third mounting surface 51A and the second mounting surface 51B (that is, the difference between the distances from the respective mounting surfaces to the above-described image pickup plane), similarly as in the electronic module described with reference to FIG. 1.

Note that, if the solid wiring board 51 is an MID board manufactured by the MID process, the first electrodes 71 and the second electrodes 72 are formed on the solid wiring board (MID board) 51 as described below. First, a component to be the solid wiring board is molded by injection molding or the like. Then, the surface of the molded component is irradiated with laser, to thereby expose or activate a catalyst in the molded body in a given region (pattern). A first metal (Cu, for example) film can be formed in the portion irradiated with the laser by non-electrolytic plating, and then a second metal (Au, for example) film can be further formed on the first metal film by electrolytic plating, to thereby improve the performance such as conductivity.

In addition, the first chip component 61 is connected, by solder, to the first electrodes 71 by a predetermined reflow soldering process.

The relay circuit board 52 is a rigid board including, on the same plane as the plane facing the MID board 51, the third electrodes 73 to be connected to the electrodes of the first electronic component (first chip component 61) connected to the first electrodes 71, and the fourth electrodes 74 to be connected to the second electrodes 72. The rigid board is an MID board, a ceramic board, or a resin multi-layer board, for example.

Incidentally, the integrated circuit 52 in the above-described first embodiment is supposed to be an image pickup device, for example. In such a case, the third mounting surface 51A and the second mounting surface 51B are substantially parallel to a surface of the image pickup device on which the electrodes 73 and 74 are aligned, and the electrodes 73 and 74, which are provided on a rear surface of the image pickup surface of the image pickup device, are electrically connected to the electrodes 71 (and the solder 81 for mounting the first chip component 61 on the electrodes 71) of the electronic component on the third mounting surface 51A and the electrodes 72 (and the solder 82 applied onto the electrodes 72) on the second mounting surface 51B. Such a configuration creates a space for the first chip component 61 under the image pickup device, which enables the second and third mounting surfaces to be fitted within the horizontally projected area corresponding to the occupancy surface for mounting the integrated circuit in a perpendicular direction.

Similarly, also in the example in which the image pickup module 30 is connected to the solid wiring board 51 through the relay circuit board 52 as described in the present second embodiment, each of the relay circuit board 52 and the solid wiring board 51 is formed to have a horizontally projected area substantially equal to the mounting area of the image pickup device when viewing the image pickup device 31 from the above-described direction perpendicular to the image pickup plane. Thus, a high-performance compact image pickup module in which various components are integrated is achieved.

In other words, the image pickup module includes the relay circuit board, which is a parallel plane, for electrically connecting the electrodes provided on the rear surface of the image pickup surface of the image pickup device to the electrodes 71 (and the soldering portion 81) of the electronic component (chip component) 61 mounted on the third mounting surface 51A (see FIG. 1) and the electrodes 72 (and the soldering portion 82) on the second mounting surface 51B (see FIG. 1). The occupancy area of the relay circuit board in the direction of the mounting surface thereof is made equal to the occupancy area of the image pickup device in the direction of the mounting surface thereof. Alternatively, the occupancy area (the lengths of the corresponding respective sides) of the relay circuit board is smaller than the occupancy area (lengths of the respective sides) of the image pickup device in the direction of the mounting surface thereof.

<Modification of Second Embodiment>

Hereinafter, description will be made on the modification of the second embodiment.

In the above-described first embodiment and second embodiment, description has been made on the configuration example in which the solid wiring board 51 includes the two mounting surfaces, which are parallel to each other and have a step therebetween, as the surfaces to which the integrated circuit 52 or the relay circuit board 52 is mounted. However, the third mounting surface 51A with the step may be configured as a plurality of surfaces having a plurality of steps.

Figure 3:
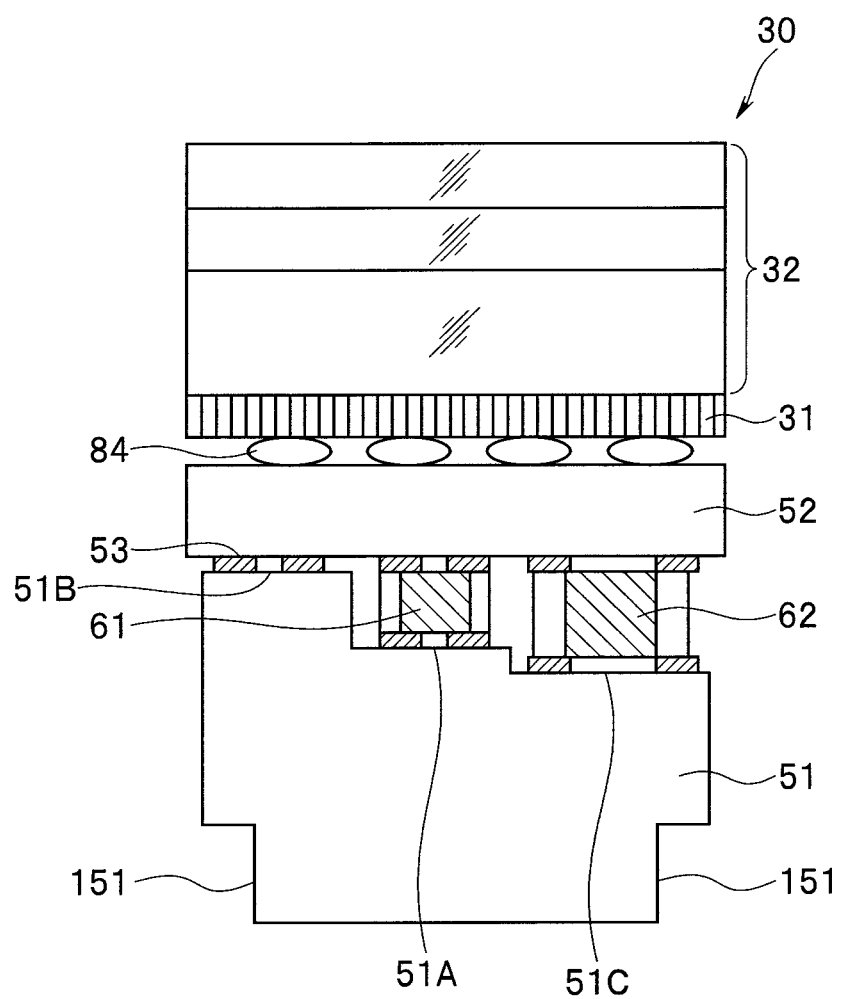
FIG. 3 is a side view showing an electronic module according to a modification of the second embodiment of the present invention.

FIG. 3 is a side view showing an electronic module according to the modification of the second embodiment of the present invention. As shown in FIG. 3, for example, a configuration example shown below can be considered as the modification of the second embodiment.

Specifically, a configuration example in which the solid wiring board 51 includes three surfaces that can be directly soldered to a rear surface which is opposite to the image pickup surface (surface on which the optical system 32 is placed) of the image pickup device 31, and on which the electrodes are aligned (shown as the soldering portions 53 in FIG. 3). The three surfaces may include a fourth mounting surface 51C, in addition to a second mounting surface 51B similar to the one in the second embodiment and a third mounting surface 51A configured to be connectable to the electrodes of the image pickup device 31 (through the relay circuit board 52 in the modification) through the first chip component 61 having a first height. The fourth mounting surface 51C is configured to be connectable to the electrodes of the image pickup device through an electronic component 62 having a second height, the electronic component 62 being different from the first chip component 61 having the first height.

In addition, a step portion 151 may be provided on the rear surface which is opposite side of the second to fourth mounting surfaces (51B, 51A, and 51C), for enabling signal lines of the image pickup device and other electronic circuits to be drawn out to the side opposite to the direction in which the image pickup device 31 performs image pickup through the optical system 32. The step portion 151 is contrived for preventing the other electronic components from protruding outward from the above-described mounting area of the image pickup device even in the case where cable lines and the like are soldered.

With the design in which the wirings are thus extended so as not to protrude outward from the mounting surface of the image pickup device 31, when the image pickup module is used for an application such as an image pickup section to be arranged in a distal end of an endoscope, the electronic module can be housed in an elongated tube, to thereby enable the diameter of the endoscope to be reduced.

Third Embodiment

As described above, the electronic module 30 according to each of the above-described embodiments is configured such that the mounting areas of all the components do not exceed the maximum mounting area in the electronic module, or the area of the electronic component occupying the largest area at the time of mounting, by the contrivance for mounting. Description will be made on the third embodiment characterized in the contrivance for miniaturizing an image pickup module 30, with reference to FIG. 4, supposing that the image pickup device will be a component that requires the largest mounting area in the image pickup module 30 in view of the conditions such as the number of pixels, the size of the pixels, etc.

Figure 4:
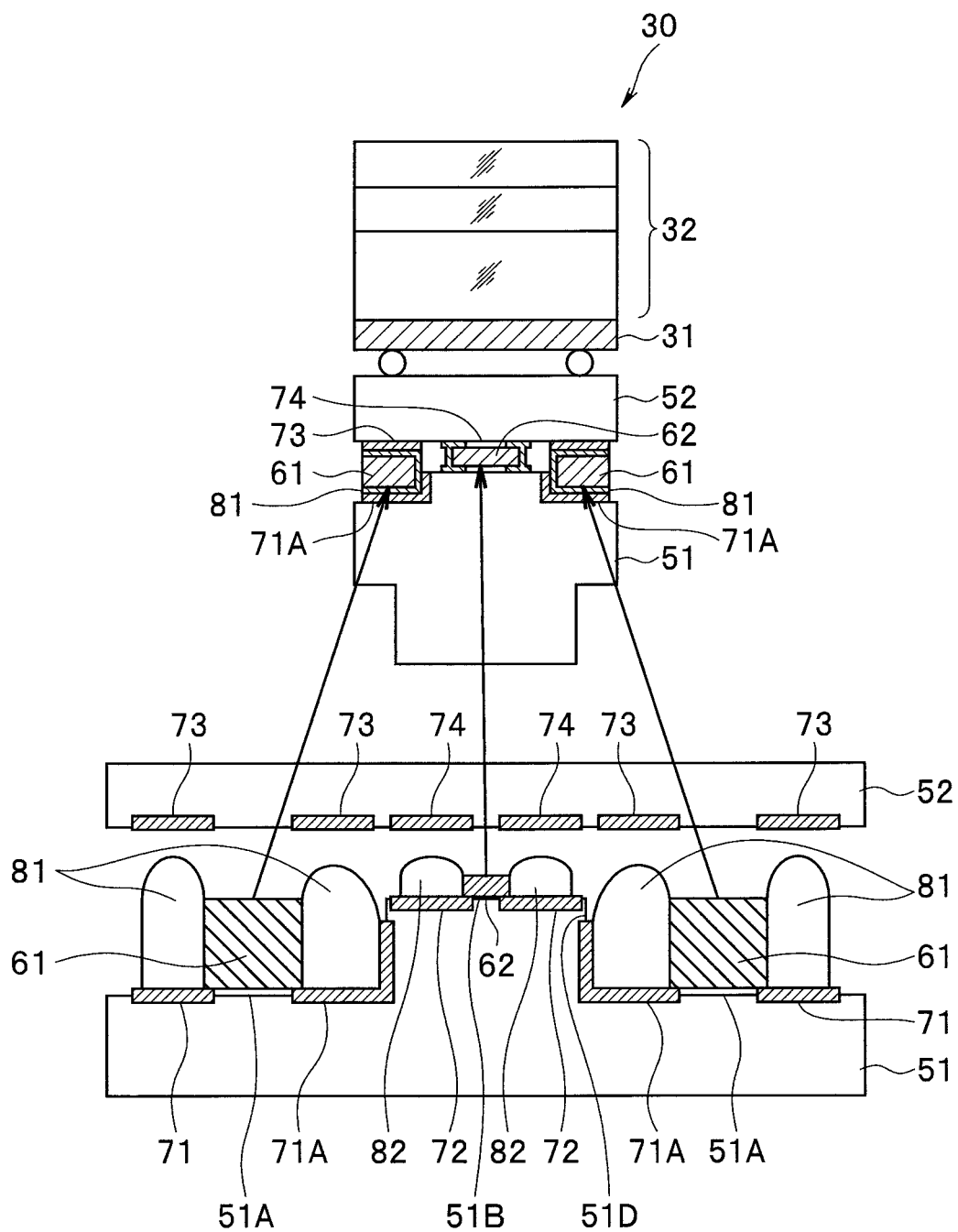
FIG. 4 is a side view showing an electronic module according to a third embodiment of the present invention.

FIG. 4 is a side view showing the electronic module according to the third embodiment of the present invention. In the third embodiment, a stacked optical system 32 is provided on the image pickup device 31. The stacked optical system 32 is configured to form an object image on the image pickup surface of the image pickup device 31. By adopting the above-described concept, the optical system is also configured to have a width and a depth (in the image pickup direction, direction orthogonal to the optical axis of the image pickup optical system, and direction horizontal to the mounting surface) so as not to exceed the occupancy area of the mounting surface of the image pickup device.

In addition, similarly as described in the first embodiment, peripheral components (chip components such as resistor, capacitor, etc.) of the image pickup device are also disposed in the space formed by the solid wiring board 51 and the relay circuit board 52 such that the peripheral components are fitted within the occupancy area of the image pickup device 31 in the direction orthogonal to the image pickup optical system. In the third embodiment, the relay circuit board 52 is a multi-layer board configured to exchange the alignment of the electrodes for signals for controlling the image pickup device or outputting image pickup signals so as to be suitable for the electrodes on the solid wiring board 51 and the electrodes for the components.

In the third embodiment, the electrodes 73 and 74 on the relay circuit board 52 are positioned such that the electrodes 73 correspond to the electrodes 71 and 71A of the solid wiring board 51 and the electrodes 74 correspond to the electrodes 72 of the solid wiring board 51. Such positioning of the electrodes enables easy solder connection. The solid wiring board 51 in the third embodiment is connected to the cable wiring patterns (to be described later) on the rear surface opposite to the mounting side of the components whose layout has been changed by the relay circuit board 52. In addition, the solid shape of the solid wiring board 51 is contrived, to thereby guide the wiring patterns to the electronic components disposed at the appropriate positions.

The third embodiment provides a contrivance such that the electronic components (chip components) 61 and 62 do not move to the outside of the occupancy area of the image pickup device by preventing the positions of the electronic components 61 and 62 from shifting during the solder connecting operation. The chip components 62 are located near the center of the module. If the amount of the solder 82 is appropriate, the chip components 62 are drawn by the surface tension of the solder to substantially the center of a pair of soldering lands (electrodes) 72 and fixed. The pair of soldering lands 72 have substantially the same pattern area and the same pattern shape so as to obtain a balanced surface tension.

On the other hand, regarding the electronic components 61, consideration is needed for a point different from the point considered for the electronic components 62. In other words, a measure is needed for preventing the electronic components 61 from shifting in the state where the solder is melted during the soldering and protruding outward from the range of the area of the image pickup device when viewing the image pickup device from the direction of the image pickup surface, as described above.

In view of such a point, the third embodiment has a feature in that the soldering patterns are extended so as to be located also on walls of side surfaces of a protruding portion provided at the center portion of the mounting surface of the solid wiring board 51, such that a pulling force acts in the direction of the protruding portion. With such a contrivance, in the state where the solder is melted, a force is generated in the direction in which each of the electronic components 61 is brought close to the protruding portion at the center portion, to thereby prevent the electronic components 61 from protruding out from the horizontally projected area under the image pickup device.

In addition, the solder at each of the soldering patterns thus provided is located at the position where each of the soldering patterns can be connected also to the electrodes of the relay circuit board 52, to thereby enable a communication with the image pickup device 31 and other components.

Figure 5:
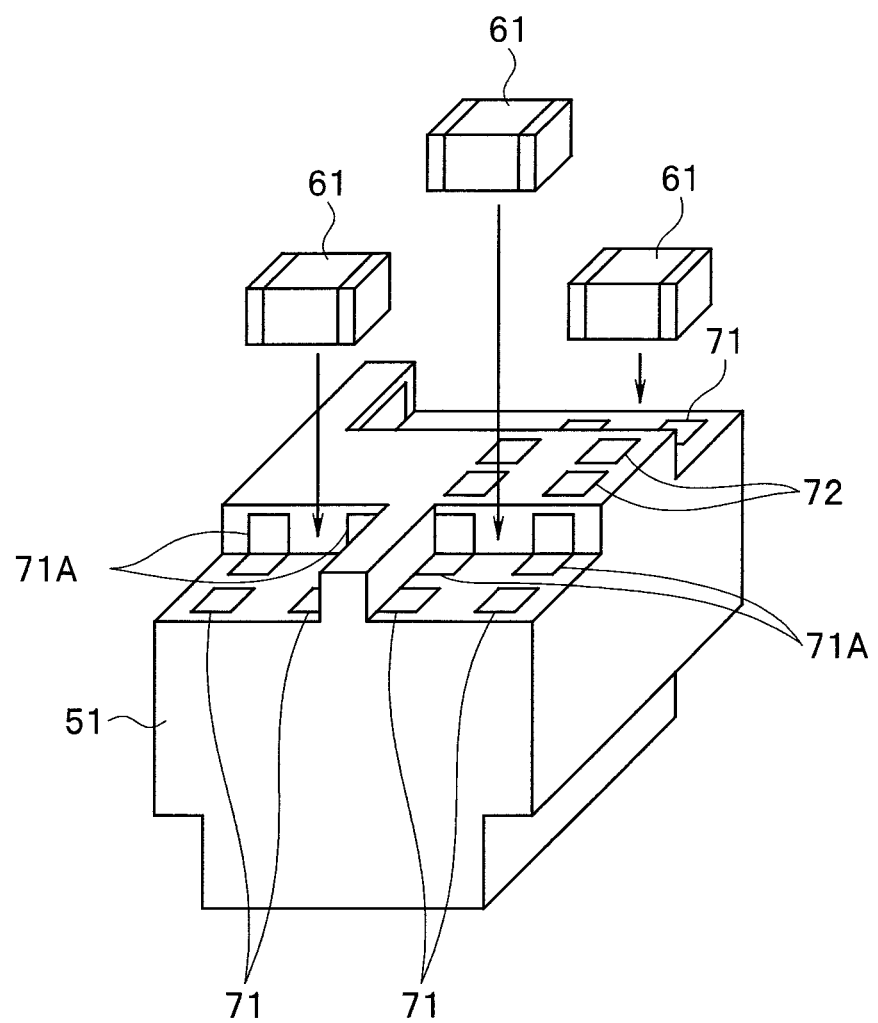
FIG. 5 is a perspective view showing an arrangement relation between a solid wiring board and electronic components in the electronic module according to the third embodiment.

FIG. 5 shows, in a perspective view, the relation between the solid wiring board 51 having the wiring patterns thus contrived and the electronic components 61 mounted on the mounting surface of the solid wiring board 51.

As shown in FIG. 5, the respective electrodes of the electronic components (chip components) 61 are mounted by the electrodes (soldering patterns) 71 and 71A provided on the solid wiring board 51 to be electrically connected. The patterns of the electrodes 71A are provided respectively on wall portions each of which is substantially perpendicular to the mounting surface. Note that each of the wall portions is formed outward from the center so as to cause the surface tension to act, when the solder is melted during the soldering, so as to prevent the components from protruding outside of the range of the solid wiring board.

The shape of the protruding portion at the center portion of the solid wiring board (MID board) is determined by providing the wall portions which exhibit the above-described effects to the respective components. In addition, recessed portions are used as spaces for housing the components.

Thus, the image pickup module 30 in the third embodiment includes the image pickup optical system 32, and achieves compact modularization of the image pickup device 31 and the peripheral components group of the image pickup device. As a result, the image pickup module 30 serves as a unit capable of outputting an image pickup signal as a result of image pickup in response to a control signal inputted to the image pickup device. Such a configuration enables easy handling in an inspection after the manufacturing, to thereby be capable of providing a compact image pickup module with a simple structure.

Figure 6:
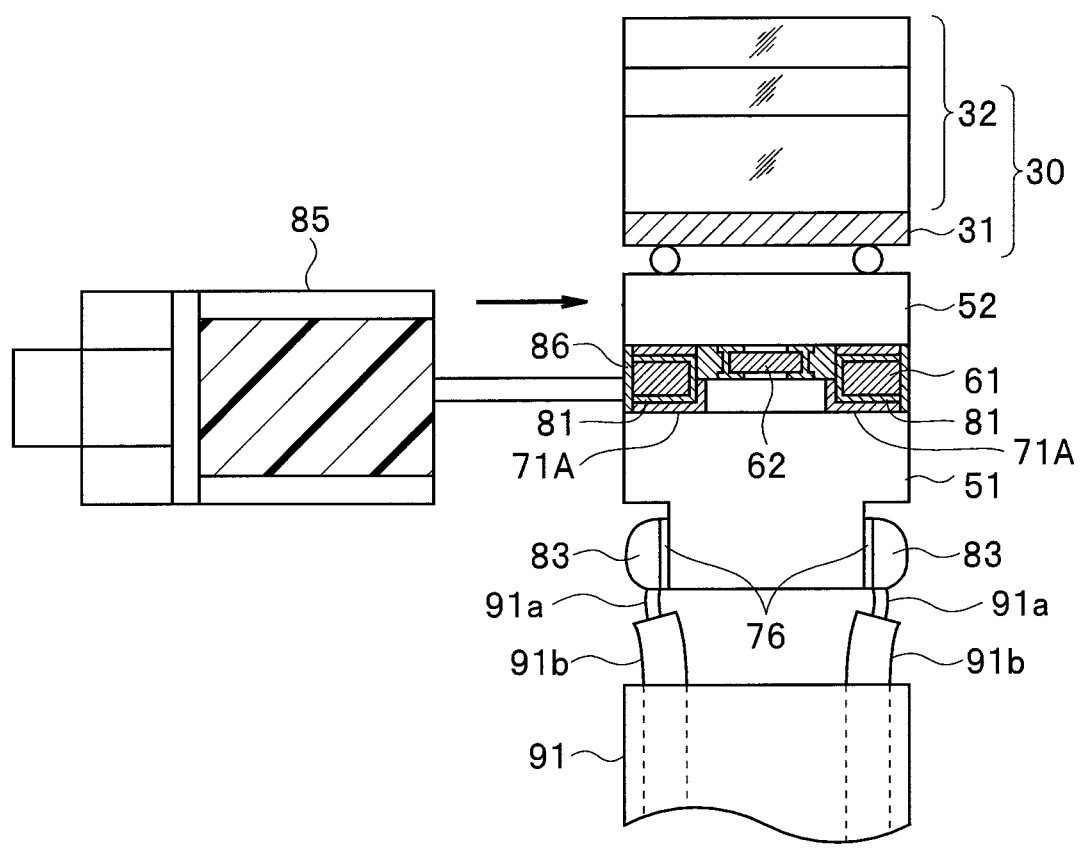
FIG. 6 is a side view showing a state where the electronic module according to the third embodiment is reinforced and a cable is further connected to the electronic module.

FIG. 6 is a side view showing a state where the electronic module according to the third embodiment is reinforced and a cable is further connected to the electronic module. As described above, the electronic module according to the third embodiment has a structure in which the image pickup optical system 32 is stacked on the side of the image pickup surface (the rear surface thereof is the mounting surface) of the image pickup device 31. The relay circuit board 52, the electronic components 61 and 62, which constitute the peripheral circuits, and the solid wiring board 51 and the like are connected on the side of the mounting surface. A cable 91 is connected so as to be fitted within the range of the occupancy area of the mounting surface and the like of the image pickup device.

A conductive wire 91a of the cable 91 is connected, by solder 83, to a soldering land pattern 76 provided on the surface opposite to the component mounting surface of the solid wiring board 51. The surface opposite to the component mounting surface of the solid wiring board 51 is formed to be recessed in consideration of the outer shape of the cable such that the cable does not protrude exceeding the occupancy area of the image pickup device.

In addition, in the third embodiment, only with the soldering as in the configurations shown in FIG. 4 and FIG. 5, for example, there is a possibility that a mechanical load is applied to the solder bonded portions or the electrodes when a predetermined stress is applied to the module. In view of such a circumstance, in the present embodiment, a gap between the relay circuit board 52 and the solid wiring board 51 is filled with a resin 86, for protecting the module. FIG. 6 illustrates a state where the resin 86 is injected by a dispenser 85 such as an injector.

Such a configuration can reduce the mechanical load to be applied to the solder bonded portions or the electrodes. As a result, even in the case where a force is applied to the module, the module can be safely protected. Filling the gap with the resin 86 can reinforce the portions around the components 61 and 62, to thereby enable a stress on these components to be reduced. Note that similar processing may be performed on a gap between the image pickup device 31 and the relay circuit board 52.

Figure 7:
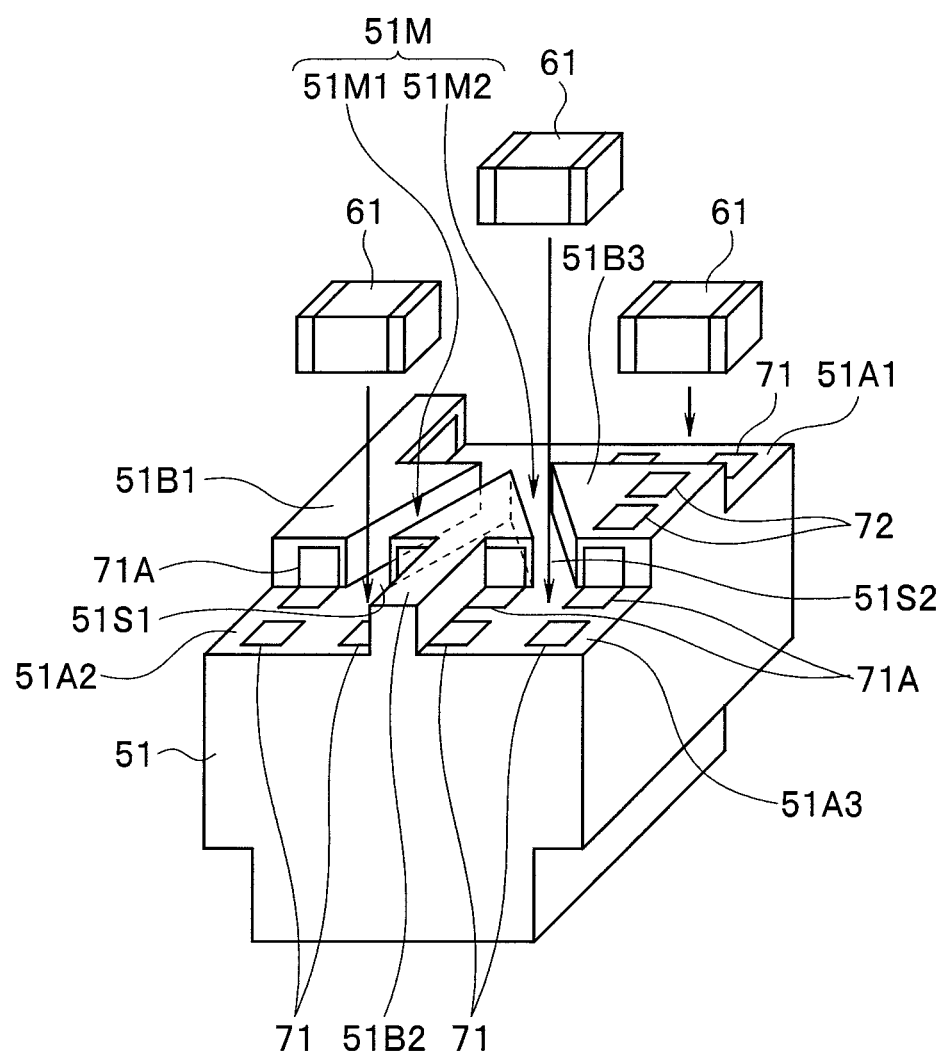
FIG. 7 is an explanatory view showing an example for facilitating injection of a resin to be filled for reducing a stress to be applied to a part of an electric connecting portion of a relay circuit board and the solid wiring board in the electronic module according to the third embodiment.

FIG. 7 is an explanatory view showing an example for facilitating injection of the resin to be filled for reducing the stress to be applied to a part of the electric connecting portion of the relay circuit board and the solid wiring board in the electronic module according to the third embodiment.

In the case of the configuration in which the second mounting surface 51B divides the third mounting surface for component mounting into a plurality of regions as shown in FIG. 5, if the resin is injected from only one site, a flow of the resin is blocked by the walls of the second mounting surface 51B. Therefore, the regions on the third mounting surface had to be filled with the resin one by one. In such a case, it had been necessary to operate the dispenser while changing the direction of the module or to prepare a plurality of dispensers. In order to save such a trouble in the manufacturing process, in the example shown in FIG. 7, a groove portion 51M (51M1, 51M2) is formed as a flow path of the resin. In such a configuration, the resin flowed from the third mounting surface 51A1 can be spread throughout the other two mounting surfaces 51A2 and 51A3, to enable the regions of the third mounting surface to be filled with the resin all at once.

With such a contrivance, each of the components 61 is disposed in a space created on the third mounting surface 51A, which is located in a direction more apart from the image pickup device than the second mounting surface 51B, and the space is filled with resin. By providing the groove portion 51M as the flow path, the adhesive area of the resin increases compared with a case where the groove portion 51M is not provided. As a result, the adhesive strength is also improved.

In such a case where the second mounting surface 51B serves as the walls to divide the third mounting surface 51A into a plurality of mounting regions, to separate the mounting regions from one another, in order to connect the plurality of separated mounting regions of the third mounting surface 51A to one another, in the third embodiment, the groove portion having bottom portions (51S1, 51S2) is provided. Each of the bottom portions has a surface a height of which is closer to that of the third mounting surface than that of the second mounting surface (for example, as shown in FIG. 7, the surfaces which are the same as the third mounting surfaces 51A2 and 51A3).

In FIG. 7, the groove portion 51M is provided at two portions (groove portions 51M1 and 51M2) so as to guide the resin to two spaces (the third mounting surfaces 51A2 and 52A3). Therefore, also the second mounting surface is divided into three regions denoted by the reference signs 51B1, 51B2, and 51B3, respectively. FIG. 7 shows an example in which a triangle shape portion, like a bow of a ship, configured to divide the flow of the resin into two flow path directions is provided on the side, where the dispenser is placed, of the second mounting surface 51B.

Such contrivance simplifies the process of injecting the resin. In addition, the resin is injected, from the third mounting surface 51A1 against which the dispenser is abutted, by such an amount that the third mounting surfaces 51A2 and 51A3, which are located at positions ahead of the flow paths, are filled with the resin moderately. Such resin injection enables the modularization to be achieved with the resin not being protruded from the mounting surfaces. Even if the resin is protruded, the resin can be easily wiped off, since the side surfaces of the solid wiring board 51 are aligned in position with the side surfaces of the mounting surface of the image pickup device 31 and the side surfaces of the optical system 32.

The image pickup module thus has an elongated structure in which the size in the width direction (the left and right direction and the depth direction in the drawings) occupied by the image pickup device including the cables is reduced. As a result, the image pickup module is easy to be housed in a thin tubular-shaped body, that is, easy to be applied to an endoscope and the like.

Figure 8A:
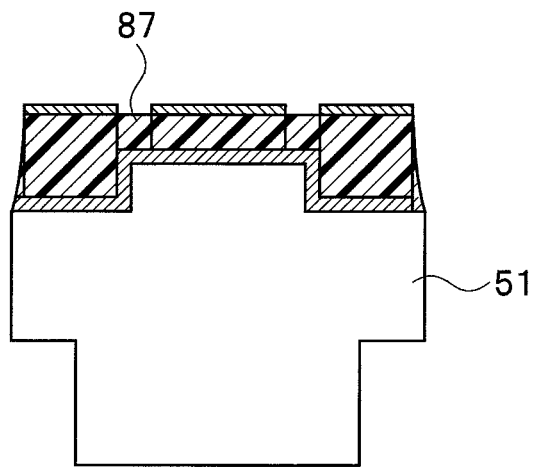
FIG. 8A shows a state where components are mounted on a mounting surface of the solid wiring board, a reinforcing resin is applied to reinforce the mounted components, and thereafter the solid wiring board is connected to the relay circuit board in the electronic module according to the third embodiment.
Figure 8B:
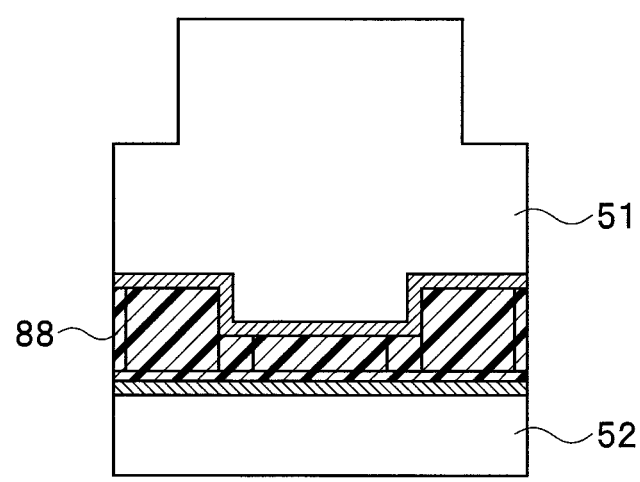
FIG. 8B shows a state where the components are mounted on the mounting surface of the solid wiring board, a reinforcing resin is applied to reinforce the mounted components, and thereafter the solid wiring board is connected to the relay circuit board in the electronic module according to the third embodiment.

FIGS. 8A and 8B are views each showing a state where the components are mounted on the mounting surface of the solid wiring board 51, the reinforcing resin is applied to reinforce the mounted components, and thereafter the solid wiring board 51 is connected to the relay circuit board 52. In this example, the components can be reinforced evenly with the resin more surely, and even if the solder connecting portions of the mounted components are remelted by reheating in the process of soldering the relay circuit board 52, the mounted components are held by the reinforcing resin, to thereby prevent the mounted components from shifting.

Figure 9:
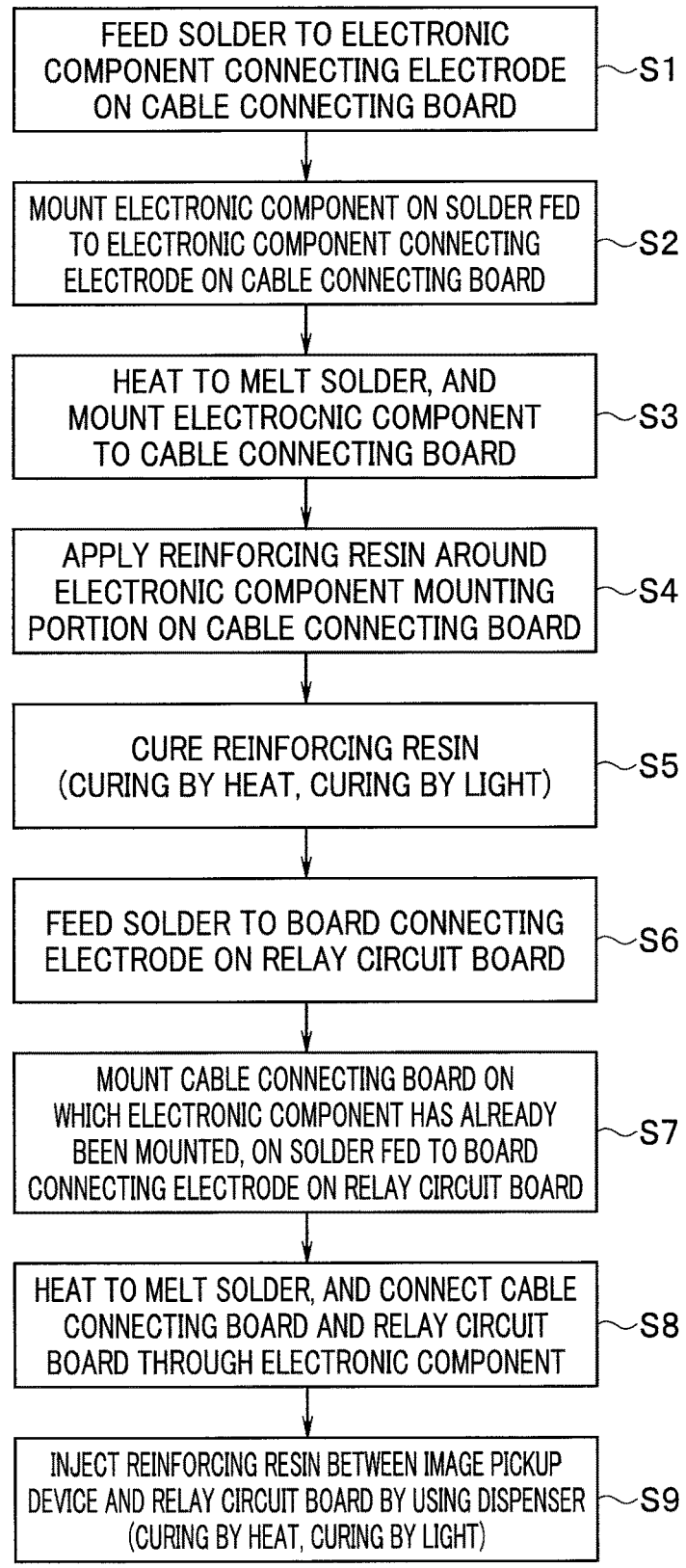
FIG. 9 is a flowchart for explaining a manufacturing process of the electronic module according to the third embodiment.

FIG. 9 is a flowchart for explaining the manufacturing process in the third embodiment. Note that the solid wiring board 51 plays an important role in connecting the image pickup device and the cable lines. Therefore, the solid wiring board is referred to as "cable connecting board".

As shown in FIG. 9, step S1 is a step of feeding solder to the soldering lands 71A in order to mount the chip components (electronic components 61 and 62) and the like to the electrodes for components on the component mounting surface of the cable connecting board (solid wiring board 51). As already described above, the components which are tall relative to the mounting surface are mounted respectively in the recessed portions. In the step S1, the solder is fed also to the patterns on the mounting surfaces having different heights and the electrodes on the side surfaces of the wall surfaces of the protruding portion, which are perpendicular to the mounting surfaces.

Step S2 is a process of mounting the electronic components such as the electronic components 61 and 62 on the parts on each of which the solder has been placed in the process in the step S1.

Step S3 indicates a process of mounting the electronic components by heating to melt the solder. In this step, the components and the soldering lands, the heights of which are made to be equal, can be fabricated, in accordance with the plane of the relay circuit board 52 to which the solid wiring board faces and is to be connected.

Step S4 is a step of applying a resin 87 between the mounted components or between the wall surfaces of the protruding portion of the solid wiring board. As shown in FIG. 8A, the resin 87 is easy to be applied onto the cable connecting board 51 due to the gravity and viscosity of the resin 87.

Step S5 is a step of curing the above-described resin. With the curing, the electronic components do not move even if the solder is heated to be melted.

Step S6 is a step of feeding the solder 81, 82 to the electrodes of the relay circuit board 52 to which the mounting surfaces of the cable connecting board 51 (solid wiring board 51) face and to be connected by the solder.

Step S7 is a step of mounting the cable connecting board on which the electronic components have already been mounted, on the solder fed to the board connecting electrodes on the relay circuit board.

Step S8 is a step of heating to melt the solder and connecting the cable connecting board and the relay circuit board through the electronic components. At this time, the positions of the components that have been already mounted and fixed by the resin do not shift by the heat. Therefore, when the components, which are out of the range of the occupancy area of the mounting surface of the image pickup device, are incorporated into the module, the area required for the module in the direction perpendicular to the image pickup optical axis direction is not changed by the components, and it is also possible to prevent the problem that the occupancy volume of the image pickup unit is changed when the image pickup unit is incorporated. As shown in FIG. 8B, a resin 88 may be further injected between the solder connecting portions for reinforcement.

Step S9 is a step of injecting the reinforcing resin between the image pickup device and the relay circuit board by using a dispenser 85. By curing the resin by heat or by light, the connecting portion between the image pickup device and the relay circuit board is reinforced.

As described above, within the horizontally projected area in the direction perpendicular to the mounting surface of the component occupying the largest area in the direction of the mounting surface in the module, the horizontally projected areas in the same direction of all other components can be fitted. Thus, each side of each of the all other components is equal to or smaller than corresponding side of the component which occupies the largest area in the module.

Next, description will be made on an endoscope system to which the electronic module according to any one of the first to third embodiments is applied, with reference to FIG. 10.

Figure 10:
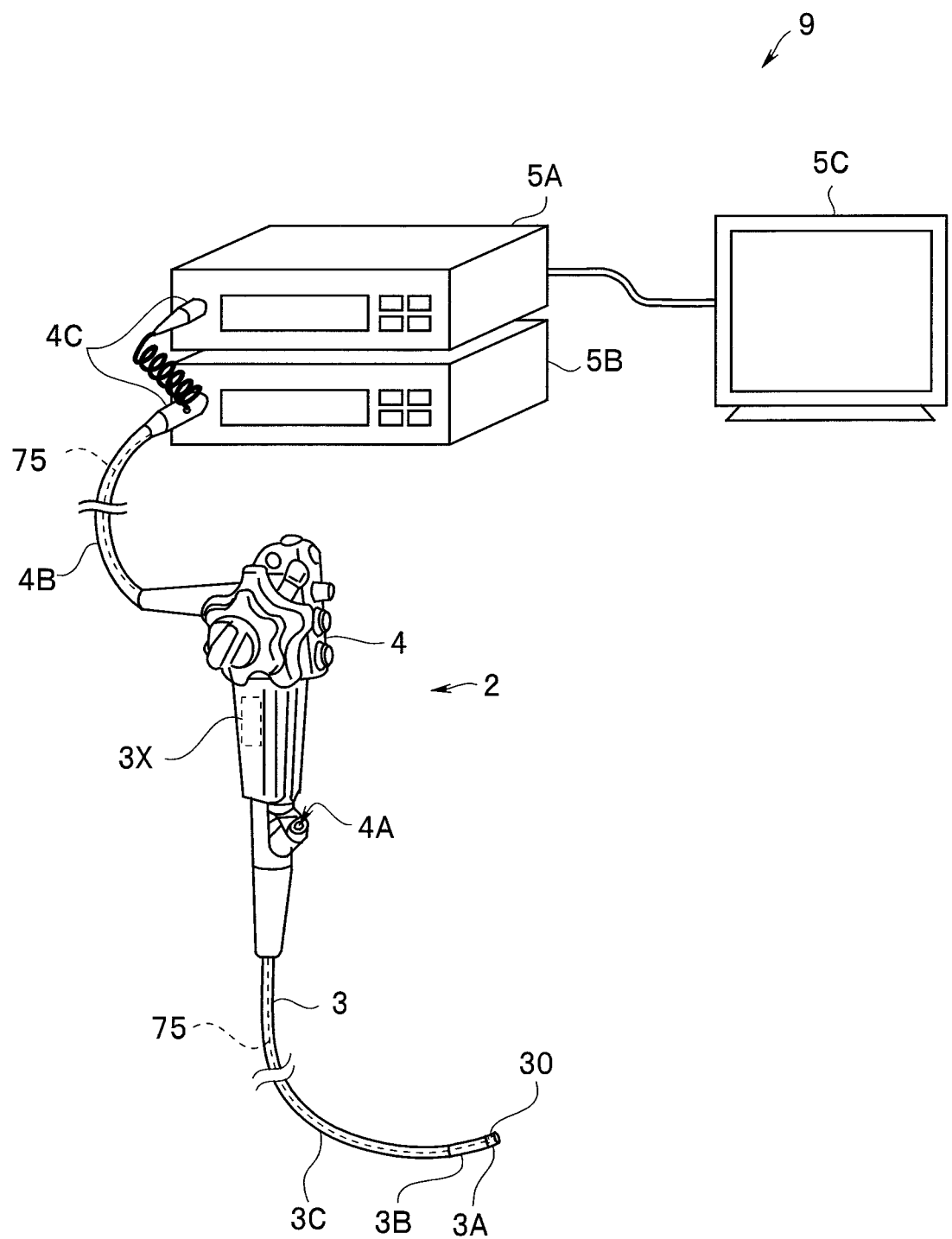
FIG. 10 shows an endoscope system to which the electronic module according to any one of the first to third embodiments is applied.

As shown in FIG. 10, an endoscope system 9 includes an endoscope 2, a processor 5A, a light source apparatus 5B, and a monitor 5C. The endoscope 2 is configured to pick up an image inside a body of a subject to output an image pickup signal, by an insertion portion 3 of the endoscope being inserted into a body cavity of the subject. The endoscope 2 includes the electronic module 30 in a distal end portion 3A of the insertion portion 3.

The endoscope 2 includes, on the proximal end side of the insertion portion 3, an operation portion 4 provided with various buttons for operating the endoscope 2. The operation portion 4 includes thereon a treatment instrument insertion port 4A of a channel through which treatment instruments such as a biopsy forceps, an electrocautery, and an inspection probe are inserted into a body cavity of a subject. In addition, a channel opening portion is disposed at the distal end of the insertion portion 3.

The insertion portion 3 includes: the distal end portion 3A in which the electronic module 30 is disposed; a bendable bending portion 3B provided continuously with the proximal end side of the distal end portion 3A; and a flexible tube portion 3C provided continuously with the proximal end side of the bending portion 3B. The bending portion 3B is configured to be bent by operating the operation portion 4.

A signal cable 75 connected to an image pickup apparatus 1 disposed in the distal end portion 3A is inserted through a universal cord 4B disposed on the side of the proximal end portion of the operation portion 4.

The universal cord 4B is connected to the processor 5A and the light source apparatus 5B through a connector 4C. The processor 5A is configured to control the whole endoscope system 9, and perform signal processing on an image pickup signal outputted from the image pickup apparatus 1, and output the image pickup signal subjected to the signal processing as an image signal. The monitor 5C displays the image signal outputted from the processor 5A.

The light source apparatus 5B includes a white LED, for example. White light emitted from the light source apparatus 5B is guided to an illumination optical system (not shown) disposed in the distal end portion 3A, through a light guide (not shown) inserted through the universal cord 4B, to illuminate an object.

The endoscope 2 includes the electronic module 30 in the distal end portion of the insertion portion, which enables reduction in the diameter size.

The present invention is not limited to the above-described embodiments, but various changes, modifications, and the like are possible without changing the gist of the present invention. For example, the above description which has been made supposing the endoscope can be applied to another apparatus by replacing the endoscope with a consumer camera, an industrial camera, a vehicle mounted camera, a monitor camera, or the like. By utilizing the feature of miniaturization in the present invention, space reduction of the image pickup unit including the cable wiring for controlling the image pickup unit and receiving a signal therefrom, can be achieved in the direction orthogonal to the direction in which the wiring is drawn out. Therefore, even in a system or layout in which a control circuit for controlling an image pickup unit is disposed at a position away from the image pickup unit disposed in a small space, a high-performance image pickup apparatus can be incorporated. In a case of an automobile, a plurality of image pickup units are mounted to meet the needs for picking up images of various locations including outside and inside of the automobile without producing a dead angle. Therefore, the miniaturization including the wiring as in the present invention is essential and facilitates the design at the time of incorporating the image pickup units. In addition, the present invention can be applied also to a mobile terminal which is required to be compact and have a light weight due to its portability, an Internet terminal such as an AI speaker, the resting place for which is preferably small, an Iot home electric appliance, and a watching camera for watching a daily life of a watched subject and ensure the safety thereof. Furthermore, the present invention provides an image pickup unit which can be easily incorporated in a mobile body such as a robot (including a cleaner and the like), a drone, and the like, which require miniaturization and light weight, and in which a center of gravity and a balance of the devices are important since the moving function is essential for these devices.

In addition, in the above description, the electronic module and the solid wiring board having a cavity portion for the image pickup unit are not limited to those created by the MID technology using the injection molding, but may be created by processing by a 3D printer or machining, for example. The material is also not limited to a resin, but may be a ceramic or a glass epoxy.

The present invention is not limited to the above-described embodiments, but various changes, modifications, and the like are possible without changing the gist of the present invention.

What is claimed is:

1. An electronic module comprising:
an integrated circuit including a first mounting surface having a first mounting area; and
a solid wiring board including a second mounting surface and a third mounting surface, the second mounting surface having a second mounting area smaller than the first mounting area, the third mounting surface having a third mounting area equal to or smaller than a difference between the first mounting area and the second mounting area, the second mounting surface and the third mounting surface being arranged within a horizontally projected area corresponding to the integrated circuit when the integrated circuit is viewed from a direction perpendicular to the first mounting surface, wherein:
both the second mounting surface and the third mounting surface face the first mounting surface of the integrated circuit, and are disposed at positions with different distances to the first mounting surface;
a surface of an electrode of an electronic component mounted in a space formed between the first mounting surface and the third mounting surface, and a surface of an electrode on the second mounting surface are arranged substantially parallel to a surface of the integrated circuit on which electrodes are aligned;
the electrode on the second mounting surface and the electrodes of the integrated circuit are electrically connected to each other; and
the electrode of the electronic component is electrically connected to the electronic component and the electrodes of the integrated circuit.

2. The electronic module according to claim 1, wherein the third mounting surface includes a fourth mounting surface and a fifth mounting surface each having a different distance to the first mounting surface of the integrated circuit, and
an electrode of an electronic component mounted on the fourth mounting surface and an electrode of an electronic component mounted on the fifth mounting surface are aligned so as to be substantially parallel to the surface of the integrated circuit on which the electrodes are aligned.

3. The electronic module according to claim 1, wherein a soldering land for the electronic component is provided on a side surface of a wall portion connecting the second mounting surface and the third mounting surface.

4. The electronic module according to claim 1, wherein the second mounting surface is arranged so as to separate the third mounting surface into a plurality of mounting regions, and
a groove portion is formed so as to connect the plurality of separated mounting regions of the third mounting surface to one another, the groove portion including a bottom portion configured such that a distance from the bottom portion to the third mounting surface is shorter than a distance from the bottom portion to the second mounting surface.

5. The electronic module according to claim 1, wherein the integrated circuit is an image pickup device,
electrodes provided on a rear surface of an image pickup surface of the image pickup device are electrically connected to the electrode of the electronic component mounted on the third mounting surface and the electrode on the second mounting surface, the third mounting surface and the second mounting surface being substantially parallel to the rear surface on which the electrodes are aligned, and
the second mounting surface and the third mounting surface are fitted in a projected area of an occupancy area for mounting the integrated circuit in a perpendicular direction.

6. The electronic module according to claim 5, further comprising
a relay circuit board configured to electrically connect the electrodes provided on the rear surface of the image pickup surface of the image pickup device to the electrode of the electronic component mounted on the third mounting surface and the electrode on the second mounting surface.

7. The electronic module according to claim 5, wherein the solid wiring board includes a recessed portion on a rear surface of the mounting surfaces facing in a direction of the image pickup device, and a metal conductive wire is connected so as to be located inside the recessed portion and within the projected area of the occupancy area for mounting the integrated circuit in the perpendicular direction.

8. A manufacturing method of an electronic module, the method being for electrically connecting a solid wiring board to a first member, the first member including a first mounting surface on which a plurality of soldering lands are arranged, the solid wiring board including a second mounting surface and a third mounting surface, on each of which a plurality of soldering lands are arranged, each of the second mounting surface and third mounting surface facing the first mounting surface and having a different distance to the first mounting surface, the method comprising:
mounting an electronic component in a space created by a difference between a distance from the second mounting surface to the first mounting surface and a distance from the third mounting surface to the first mounting surface;
fixing the electronic component mounted in the space by a resin; and
electrically connecting the soldering lands on the first mounting surface, the soldering lands on each of the second mounting surface and the third mounting surface, and an electrode of the electronic component.

9. An electronic module comprising:
an image pickup device connected to an objective optical system;
a relay circuit board connected to the image pickup device and including an external connecting terminal;
a cable connecting board connected to the relay circuit board and including a transmission cable connecting terminal; and
a transmission cable connected to the cable connecting board, wherein:
the relay circuit board and the cable connecting board are connected to each other through a first electronic component;
the first electronic component includes a plurality of electronic components each having a different size;
the cable connecting board includes a plurality of planes each having a different distance to a surface of the relay circuit board to which the cable connecting board faces;
an electronic component mounting electrode and a board connecting electrode are disposed on each of the planes;
a second electronic component is mounted on an electronic component mounting electrode of the relay circuit board;
a surface of the board connecting electrode and a surface of a relay-circuit-board-side electrode of the first electronic component are located on a substantially same surface; and the board connecting electrode and the relay-circuit-board-side electrode of the first electronic component are connected to a board connecting electrode of the relay circuit board.

10. An endoscope comprising an electronic module, the electronic module comprising:
- an integrated circuit including a first mounting surface having a first mounting area; and
- a solid wiring board including a second mounting surface and a third mounting surface, the second mounting surface having a second mounting area smaller than the first mounting area, the third mounting surface having a third mounting area equal to or smaller than a difference between the first mounting area and the second mounting area, the second mounting surface and the third mounting surface being arranged within a horizontally projected area corresponding to the integrated circuit when the integrated circuit is viewed from a direction perpendicular to the first mounting surface, wherein:

both the second mounting surface and the third mounting surface face the first mounting surface of the integrated circuit, and are disposed at positions with different distances to the first mounting surface;

a surface of an electrode of an electronic component mounted in a space formed between the first mounting surface and the third mounting surface, and a surface of an electrode on the second mounting surface are arranged substantially parallel to a surface of the integrated circuit on which electrodes are aligned;

the electrode on the second mounting surface and the electrodes of the integrated circuit are electrically connected to each other; and the electrode of the electronic component is electrically connected to the electronic component and the electrodes of the integrated circuit.

\* \* \* \* \*